(12) United States Patent
LaRue et al.

(10) Patent No.: US 11,266,775 B1
(45) Date of Patent: *Mar. 8, 2022

(54) SUCTION DEVICE FOR MEDICAL USE IN REMOVING MATERIAL FROM A SURGICAL SITE OR SIMILAR

(71) Applicant: A LaRue Company, Winston-Salem, NC (US)

(72) Inventors: Angela Vargo LaRue, Winston-Salem, NC (US); Charles Channing LaRue, Winston-Salem, NC (US); Paul Bradley Forrest, Cary, NC (US)

(73) Assignee: A LaRue Company, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,063

(22) Filed: Jul. 6, 2020

Related U.S. Application Data

(63) Continuation of application No. 16/379,832, filed on Apr. 10, 2019, now Pat. No. 10,702,635.

(51) Int. Cl.
  *A61M 1/00* (2006.01)
  *A61F 2/12* (2006.01)
  (Continued)

(52) U.S. Cl.
  CPC ........... *A61M 1/76* (2021.05); *A61B 17/3468* (2013.01); *A61F 2/12* (2013.01); *A61M 1/00* (2013.01); *A61M 1/0001* (2013.01); *A61M 1/0023* (2013.01); *A61M 1/0058* (2013.01); *A61M 1/64* (2021.05); *A61M 1/71* (2021.05); *A61M 1/77* (2021.05); *A61M 1/84* (2021.05); *A61M 39/20* (2013.01); *A61M 39/24* (2013.01);
  (Continued)

(58) Field of Classification Search
  CPC ........ A61M 1/0001; A61M 1/00; A61M 1/76; A61M 1/84; A61M 1/64; A61M 1/71; A61M 1/77; A61M 39/20; A61M 39/24; A61M 2205/3379; A61M 2205/586; A61B 2217/005; A61B 2090/062
  See application file for complete search history.

(56) References Cited

U.S. PATENT DOCUMENTS

| 4,465,485 A | 8/1984 | Kashmer et al. |
| 4,597,594 A | 7/1986 | Kacalieff et al. |

(Continued)

FOREIGN PATENT DOCUMENTS

| WO | 2018226726 A1 | 12/2018 |

OTHER PUBLICATIONS

USPTO, Non-Final Office Action in U.S. Appl. No. 16/79,832 dated Jul. 5, 2019.

(Continued)

*Primary Examiner* — Dinah Baria
(74) *Attorney, Agent, or Firm* — NK Patent Law

(57) ABSTRACT

A device for evacuating a surgical site of a patient includes a container that defines a first end having a tapered surgical site engaging surface and a second end having a pressure source engaging surface. The first end defines a tapered cross-section configured for being engageably received within an opening at the surgical site. In operation, vacuum pressure is applied to the second end in order to create a vacuum within the container to evacuate fluids from the surgical site.

13 Claims, 8 Drawing Sheets

(51) Int. Cl.
*A61B 17/34* (2006.01)
*A61M 39/20* (2006.01)
*A61M 39/24* (2006.01)
*A61B 90/00* (2016.01)

(52) U.S. Cl.
CPC ... *A61B 2090/062* (2016.02); *A61B 2217/005* (2013.01); *A61M 2205/3379* (2013.01); *A61M 2205/586* (2013.01)

(56) References Cited

U.S. PATENT DOCUMENTS

| | | | |
|---|---|---|---|
| 6,299,033 | B1 | 10/2001 | VerWeyst et al. |
| 2007/0173736 | A1* | 7/2007 | Feuer ................. A61B 10/0291 600/562 |
| 2017/0274125 | A1 | 9/2017 | Minskoff et al. |
| 2019/0209290 | A1 | 7/2019 | Yousif et al. |

OTHER PUBLICATIONS

USPTO, Final Office Action in U.S. Appl. No. 16/379,832 dated Dec. 16, 2019.

* cited by examiner

SUCTION DEVICE FOR MEDICAL USE IN REMOVING MATERIAL FROM A SURGICAL SITE OR SIMILAR

CROSS-REFERENCE TO RELATED APPLICATION

This application is a continuation of U.S. patent application Ser. No. 16/379,832, filed on Apr. 10, 2019, issuing as U.S. Pat. No. 10,702,635 on Jul. 7, 2020, the entire contents of which are hereby incorporated herein by reference.

TECHNICAL FIELD

The present invention relates to a device for medical use in removing material from a surgical site or similar, and, more particularly, towards a device having a container configured for evacuating material from a surgical site in an efficient and cleanly manner.

BACKGROUND

Breast implants are becoming more and more popular in the United States and elsewhere. A breast implant is a prosthesis that may be used for changing the size, shape, and contour of a human breast. Breast implants are implanted under the breast tissue or under the chest muscle to increase breast size (augmentation), to rebuild breast tissue after mastectomy or other damage to the breast (reconstruction), or to correct congenital defects in the chest wall. They are also used in revision surgeries, which correct or improve the result of an original surgery.

Breast implants are available in many different forms; saline-filled breast implants, in which an implant shell is filled with sterile salt water, and silicone-filled breast implants, in which the implant shell is filled with a silicone gel. Both types have a silicone outer shell. They vary in size, shell thickness, shell surface texture, and shape (contour).

Rupturing of silicone breast implants can result after placement into the human body. When this occurs in a saline breast implant, it deflates, meaning the saltwater (saline) solution leaks from the shell. When a silicone gel-filled implant ruptures, the gel may remain in the shell or in the scar tissue that forms around the implant. Silicone gel that leaks outside the capsule surrounding the implant may travel (migrate) away from the breast. The leaked silicone gel may cause lumps to form in the breast or in other tissue. It may be difficult or impossible to remove silicone gel that has traveled to other parts of the body. Ruptured silicone breast implants can cause breast pain or changes in the contour or shape of the breast. After rupture, the implant is usually removed. Removal after rupture is a time consuming, tedious and difficult process. Typically, such removal is performed by manual extraction utilizing surgical sponges or a crude bottle suction device that has poor performance and is susceptible to infection and other medical complications.

Accordingly, there is a need for a manner or device to aid in this removal process.

SUMMARY

This summary is provided to briefly introduce concepts that are further described in the following detailed descriptions. This summary is not intended to identify key features or essential features of the claimed subject matter, nor is it to be construed as limiting the scope of the claimed subject matter.

According to one or more embodiments, a device for evacuating a surgical site of a patient includes a container that defines a first end having a surgical site engaging surface; and a second end having a pressure source engaging surface. The first end defines a tapered cross-section configured for being engageably received within an opening at the surgical site. In operation, vacuum pressure is applied to the second end in order to create a vacuum within the container to evacuate fluids from the surgical site.

According to one or more embodiments, the tapered cross-section of the first end is rotatable relative to the container and a longitudinal extending through the tapered cross-section extends at an angle relative to the container.

According to one or more embodiments, the container defines a substantially flat surface, wherein the container defines a lay flat orientation in which the container is positioned such that the substantially flat surface engages a proximal support surface.

According to one or more embodiments, the tapered cross-section of the first end defines a graduated series of ridges extending circumferentially thereabout in order to indicate depth of insertion of the tapered cross-section into the surgical site, and to provide sealing engagement with the surgical site.

According to one or more embodiments, the tapered cross-section defines a circumferentially extending recess at a base thereof for receiving a cap and the cap defines a lip for engaging with the recess.

According to one or more embodiments, the second end defines a connector that is selectively engageable therewith, the connector configured for fluidly engaging with the pressure source.

According to one or more embodiments, the pressure source is a vacuum.

According to one or more embodiments, the connector defines a backflow valve positioned therewithin.

According to one or more embodiments, the container is translucent. According to one or more embodiments, the device defines volume markings thereon for indicating a volume of material contained therein.

According to one or more embodiments, the container defines a depression along a length thereof for providing a gripping surface.

The above summary is to be understood as cumulative and inclusive. The above described embodiments and features are combined in various combinations in whole or in part in one or more other embodiments.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

The foregoing summary, as well as the following detailed description of various embodiments, is better understood when read in conjunction with the appended drawings. For the purposes of illustration, there is shown in the drawings exemplary embodiments; however, the present invention is not limited to the specific methods and instrumentalities disclosed. In the drawings.

DETAILED DESCRIPTIONS

Figure 1:
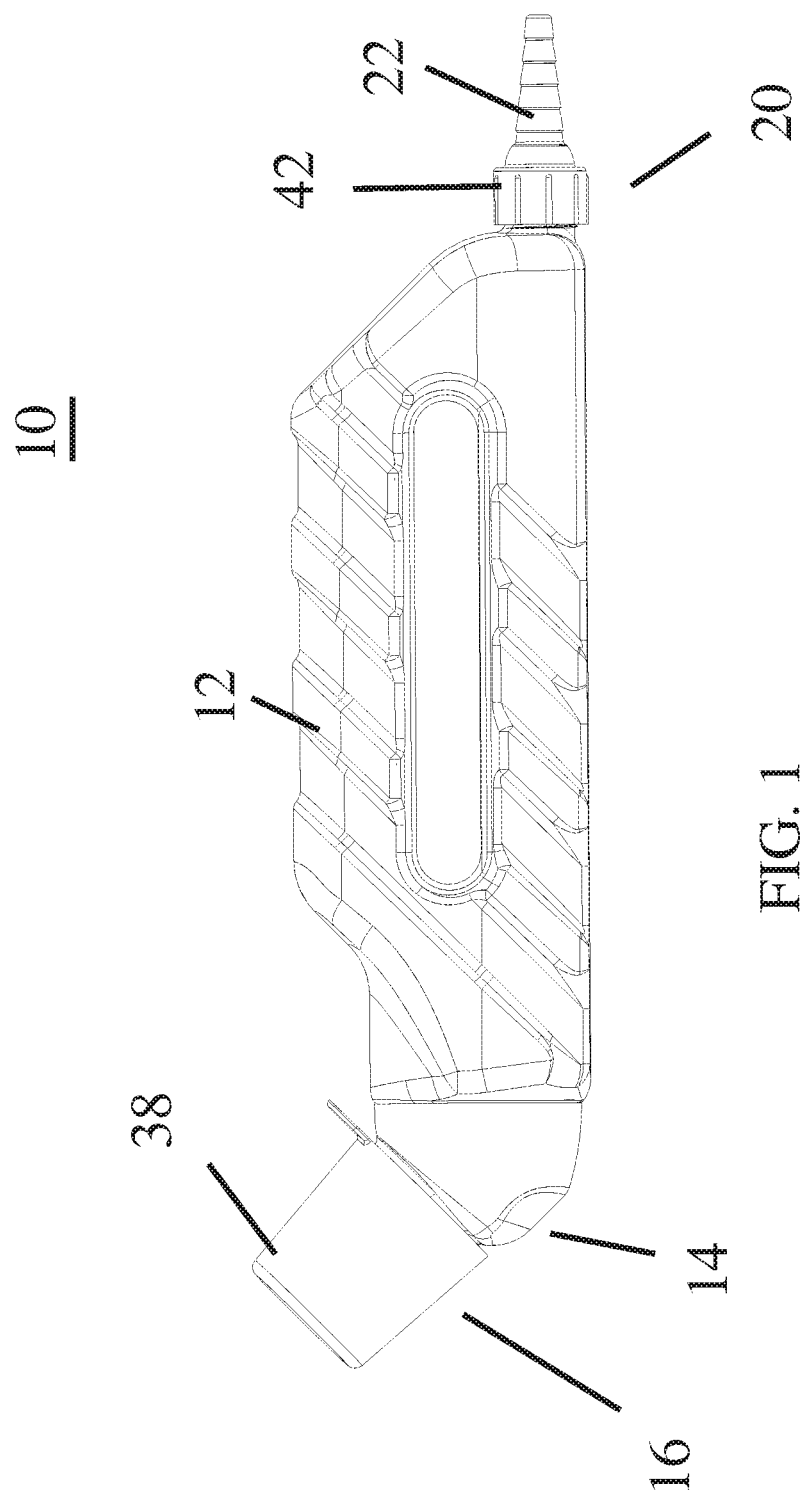
FIG. 1 is a side view of a device for evacuating a surgical site of a patient according to one or more embodiments disclosed herein.

Throughout the drawings there is illustrated a device for evacuating a surgical site of a patient, where the device is generally designated as 10. With particular initial reference to FIGS. 1 and 2, the device 10 includes a container 12 as illustrated, though many other appropriately configured shapes and sizes may be employed. The container 12 defines a first end 14 having a surgical site engaging surface 16. The container 12 defines a second end 20 having a pressure source engaging surface 22. The first end 14 defines a tapered cross-section 24 configured for being engageably received within an opening at the surgical site, as better illustrated in FIG. 2. Use of the device 10 is further illustrated with reference to FIG. 6 as will be described in greater detail. In operation, vacuum pressure is applied to the second end 20 in order to create a vacuum within the container 12 to evacuate fluids from the surgical site. A cap 38 may be provided at the first end 14 and will be described with further reference herein.

Figure 7:
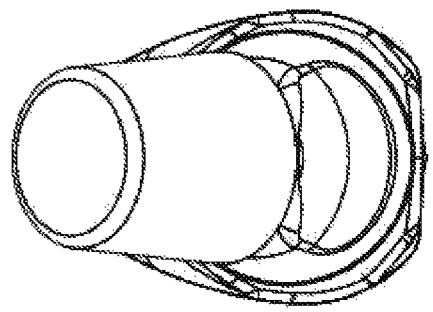
FIG. 7 is a front view of the device in a lay flat orientation according to one or more embodiments disclosed herein.
Figure 8:
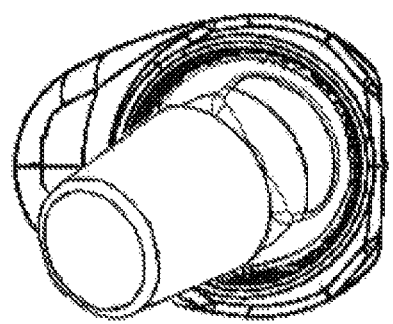
FIG. 8 is a front view of the device where a first end is shown rotated relative to the view shown in FIG. 7 in order to provide a more ergonomic approach.

One advantageous aspect of the device illustrated herein is that the tapered cross-section 24 of the first end 14, where the first end 14 is rotatable relative to the container 12 as illustrated in one embodiment in FIG. 7 and FIG. 8. A longitudinal 26 extends through the tapered cross-section 24 at an angle relative to the container 12. In the embodiment illustrated in FIG. 2, the angle is shown as about 45 degrees, but any appropriately configured angle may be employed.

Figure 2:
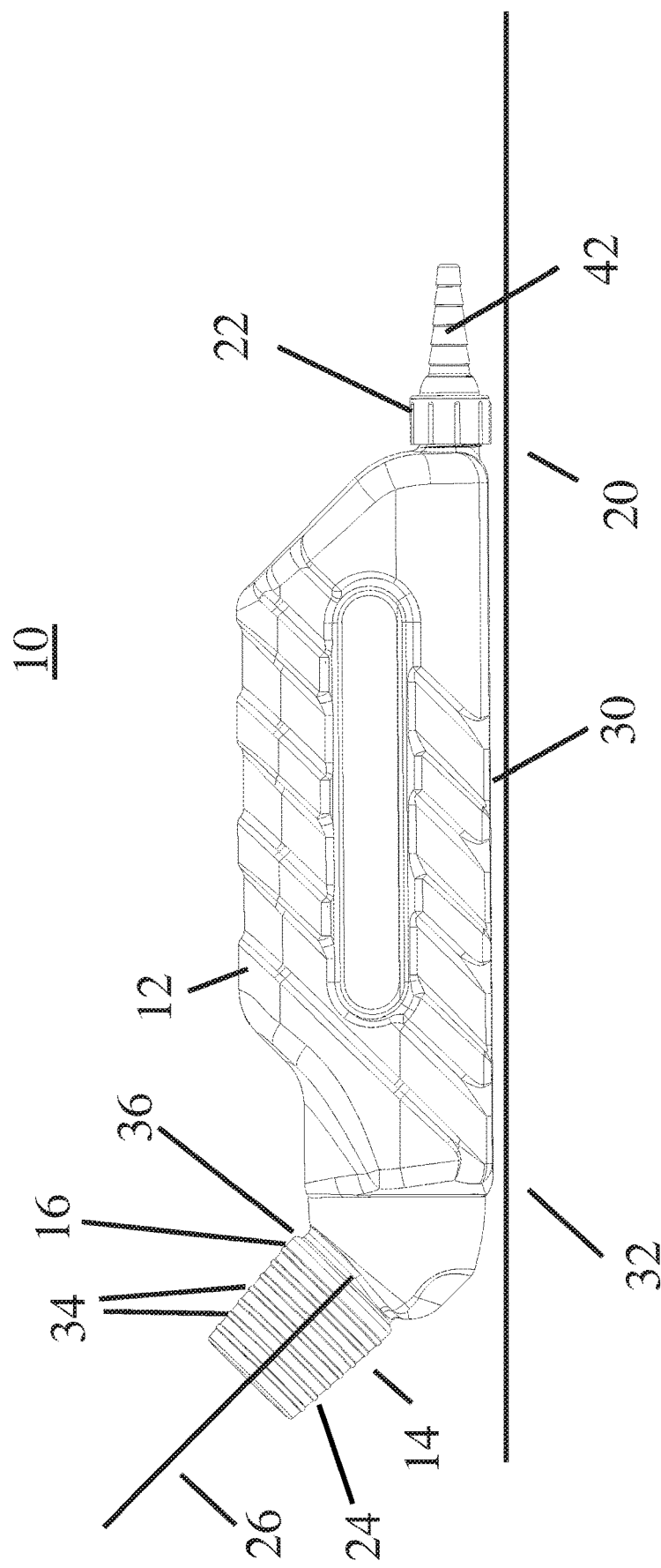
FIG. 2 is a side view of the device shown with a cap removed and sitting on a proximal surface in a lay flat position according to one or more embodiments disclosed herein.
Figure 3:
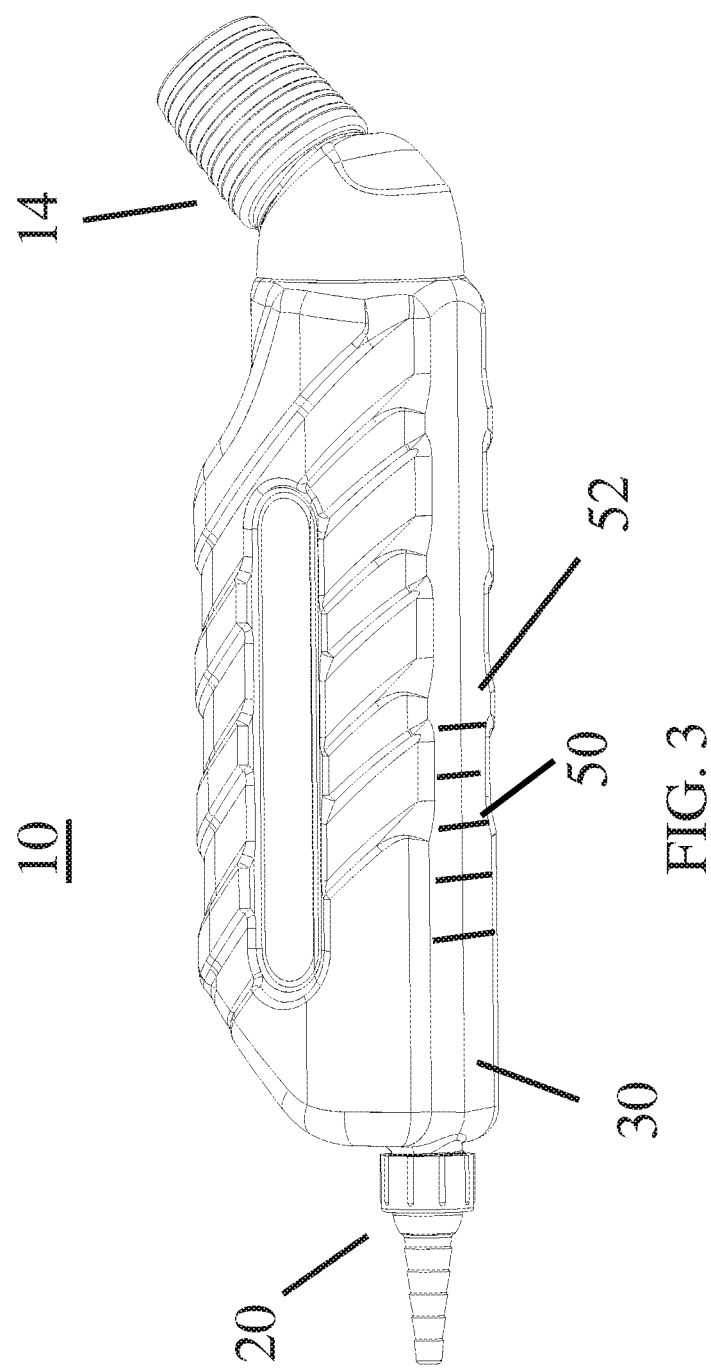
FIG. 3 is a bottom facing view of the device shown in FIG. 1 where the orientation is rotated 180 degrees and the bottom facing surface is better illustrated according to one or more embodiments disclosed herein.
Figure 4:
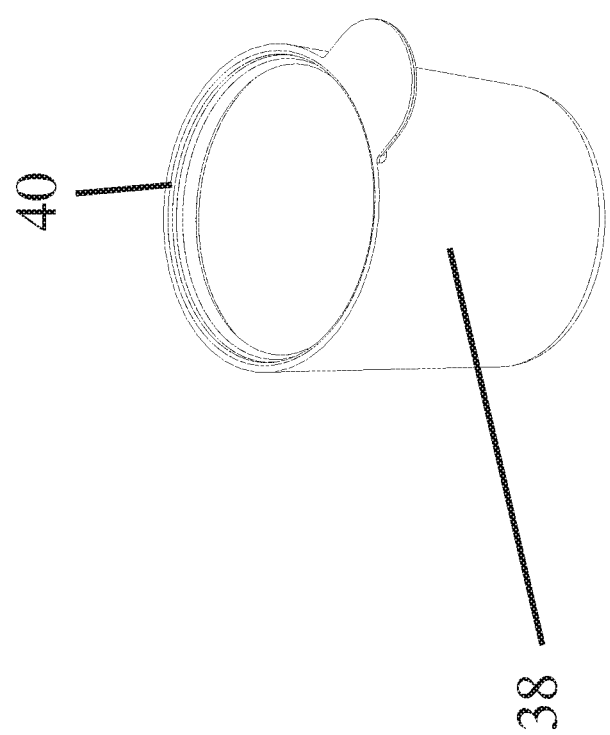
FIG. 4 is a perspective view of a cap for use with the device according to one or more embodiments disclosed herein.

As illustrated in FIG. 2 and with further reference to FIG. 3, the container 12 defines a substantially flat surface 30, wherein the container defines a lay flat orientation in which the container is positioned such that the substantially flat surface engages a proximal support surface 32. In this manner, the container 12 is rested onto a working table or surface about flat surface 30, and is naturally returned to the lay flat orientation because of the angle that the user grips the device 10 and the shape thereof. This reduces the chances that the container 12 will be inadvertently displaced from the table or support surface. Furthermore, unlike most elongate containers where the container is oriented vertically along its longitudinal axis, this container is oriented horizontally along its longitudinal axis, and as such, the substantially flat surface 30 is more advantageous. The lay flat orientation is even more advantageous here as it maintains the first end 14, which is offset at an angle, away from the table or support surface 32, thus reducing contamination and the like.

Figure 6:
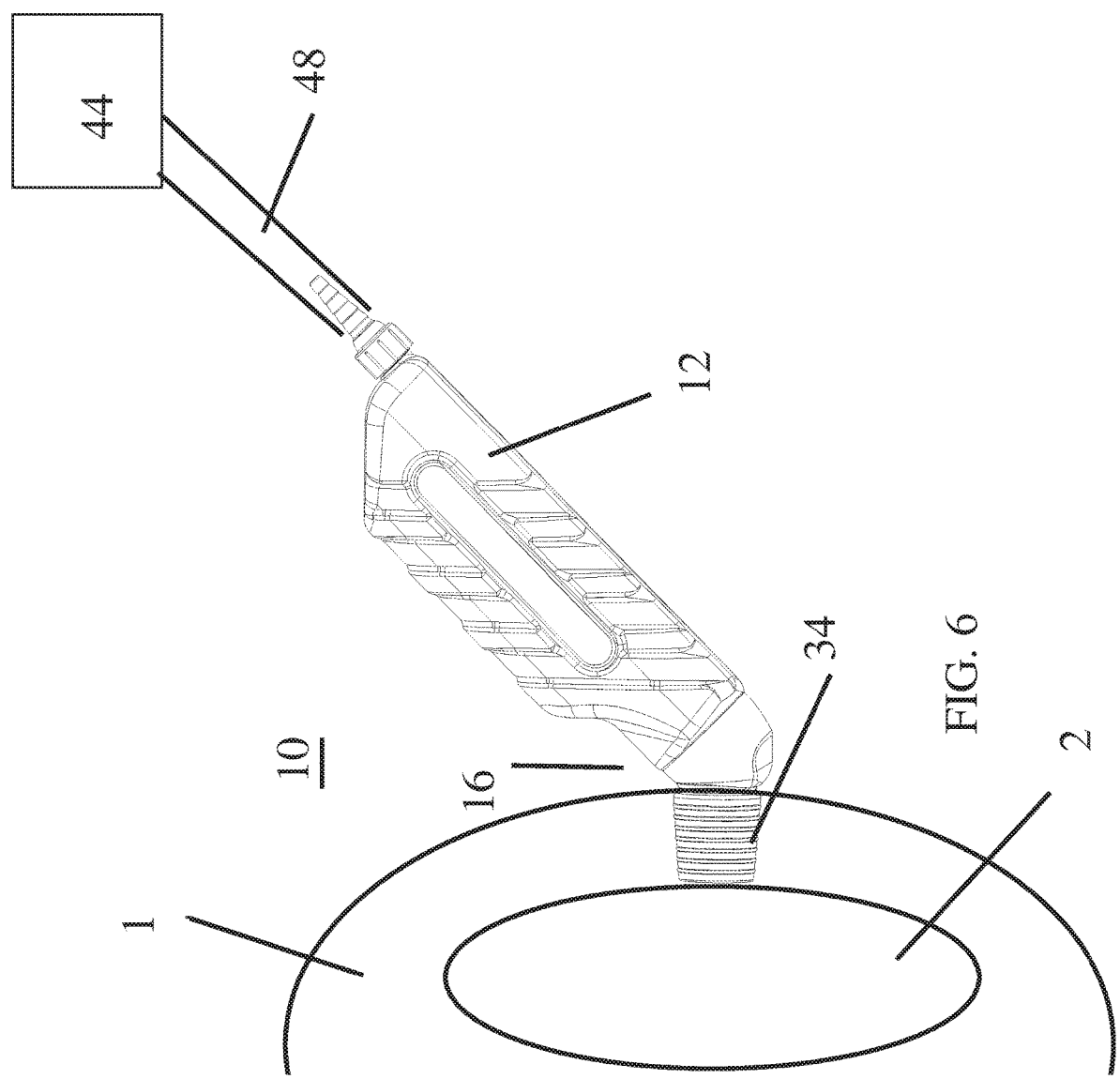
FIG. 6 is a perspective view of the device in use being illustrated for removing a breast implant from a patient according to one or more embodiments disclosed herein.

As illustrated in FIG. 2 and with further reference to FIG. 6, the tapered cross-section 24 of the first end 14 defines a graduated series of ridges 34 extending circumferentially thereabout in order to indicate depth of insertion of the tapered cross-section into the surgical site, and to provide sealing engagement with the surgical site. Thus, as illustrated in FIG. 6, the device 10 is illustrated within a breast 1 to remove an implant 2, and the device is illustrated being at about the seventh graduated ridge 34, thus indicating a certain depth of insertion and width of insertion due to the tapered shape. Relatedly, the tapered cross-section 24 may define a circumferentially extending recess 36 at a base thereof for receiving the cap 38. The cap 38 may define a corresponding lip 40 for engaging with the recess.

Figure 5:
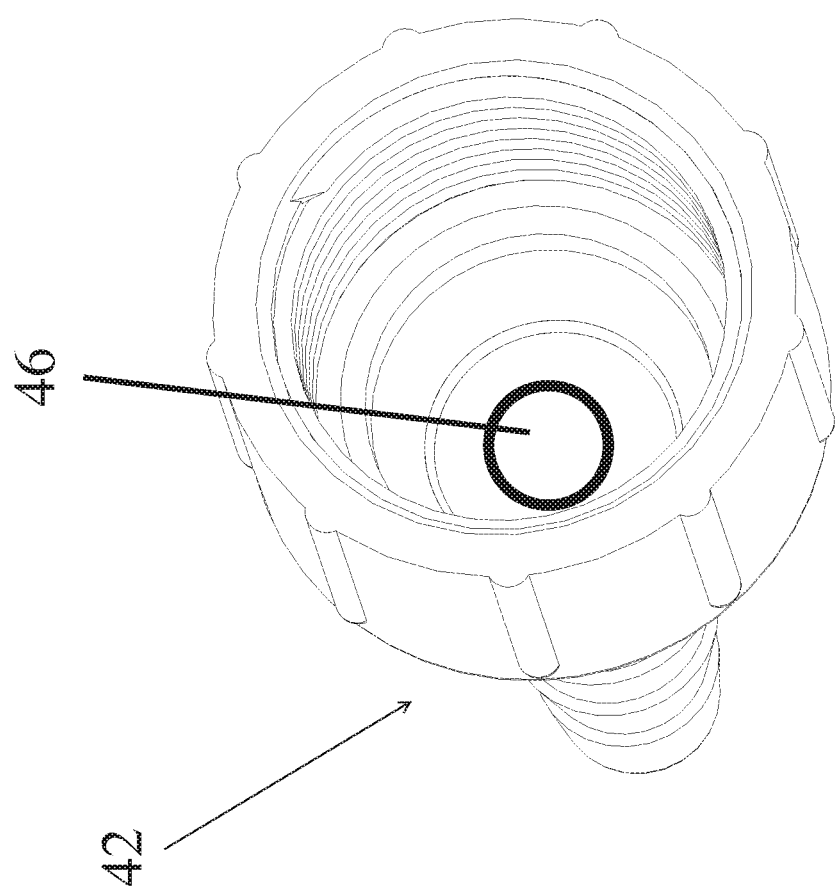
FIG. 5 is a perspective view of a pressure connector for connecting the device to a vacuum or pressure source according to one or more embodiments disclosed herein.

With reference to FIG. 5 and FIG. 6, the second end 20 defines a connector 42 that is selectively engageable therewith. The connector 42 is configured and illustrated receiving a pressure hose 48 that is coupled to a pressure source 44. The pressure source 44 may provide vacuum sources through hose 48 to connector 42. The connector 42 may include a backflow valve 46 that is provided within the connector 42. The connector 42 may be threadably engaged with second end 20 so that connector 42 may be selectively replaced by threading the connector 42 onto second end 20. In this manner, when connector 42 needs replacing, or a different sized backflow valve 46 or similar is desired, a different connector 42 is subsequently threaded onto second end 20.

As illustrated with reference to FIG. 3, the container 12 defines volume markings 50 thereon for indicating a volume of material contained therein. Additionally, the container 12 may define a depression 52 along a partial length thereof for providing a gripping surface.

As illustrated in FIG. 6, use of the device 10 includes many advantageous aspects. First the cap 38 may be removed, exposing the first end 14 and tapered portion 24. A desired angle of orientation of the tapered portion 24 relative to container 12 may then be selected. For example, a right handed physician or provider removing a ruptured implant from a left sided incision site of a left breast may desire to rotate the first end 14 clockwise (while facing towards the first end 14) to a desired angle. This is well illustrated with reference to FIG. 7 and FIG. 8. The first end 14 may further define a locking mechanism to lock engagement of the first end 14 to the container 12 at a desired angle. The container 12 may then be fluidly engaged with hose 48 and to pressure source 44. Hose 48 may also come pre-coupled to connector 42 and connector 42 is then threadably coupled to container 12. A desired pressure may be selected at pressure source 44. The pressure may also be ramped up or down depending on preferences. The first end 14 is inserted into the incision to a desired depth by monitoring the depth indicator lines formed by ridges 34. Removal of the ruptured implant is then carried out. The physician or provider is able to visualize whether complete removal has occurred by viewing the graduated volume markings 50 on the container 12. The cap 38 is then placed back on the container 12 and the container 12 is then either taken for further testing of material thereon, or the container 12 is disposed. The container 12 may define a generally oblong cross-section which provides improved ergonomics for the device 10.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A device for evacuating a surgical site of a patient for removing a breast implant, the device comprising:
   a container having a first end and an opposite second end, the container defining a longitudinal axis extending through the first end and second end; and
   a connector engaged with the second end of the container, the connector configured for coupling to a vacuum source to apply vacuum to an interior of the container,
   wherein the first end includes a tapered engaging surface for being received within an opening at the surgical site thereby providing sealing engagement between the surgical site and interior of the container,
   wherein, in surgical operation the tapered engaging surface provides sealing engagement with the surgical site when inserted into the opening, and vacuum is applied to the container via the connector to evacuate the breast implant from the surgical site, and
   wherein the tapered engaging surface extends at an angle relative to the longitudinal axis of the container, and wherein the first end is rotatable relative to the container during surgical operation such that an orientation of the tapered engaging surface is selectable during surgical operation.

2. The device according to claim 1, wherein the container defines a substantially flat surface, which is parallel to the longitudinal axis, for positioning the container on a support surface such that the longitudinal axis is horizontal.

3. The device according to claim 1, wherein the connector comprises a backflow valve.

4. The device according to claim 1, wherein the tapered engaging surface comprises a base that defines a circumferentially extending recess for engaging a cap, the cap defining a lip for engaging the recess.

5. The device according to claim 1, wherein the container is translucent.

6. The device according to claim 1, wherein the container comprises volume markings for indicating a volume of material contained therein.

7. The device according to claim 1, wherein the container defines a depression along a length thereof for providing a gripping surface.

8. The device according to claim 1, wherein the tapered engaging surface defines a graduated series of circumferentially extending ridges.

9. The device according to claim 8, wherein, in operation the ridges indicate depth of insertion of tapered engaging surface into the opening at the surgical site.

10. The device according to claim 8, wherein, in operation the ridges provide sealing engagement with the surgical site when the tapered engaging surface is inserted into the opening at the surgical site.

11. The device according to claim 8, wherein the ridges permit removal of the tapered engaging surface from the opening at the surgical site.

12. The device according to claim 8, wherein the ridges permit removal of the tapered engaging surface from the opening without injury.

13. The device according to claim 8, wherein the ridges have rounded edges permitting insertion and removal of the tapered engaging surface into and from the opening at the surgical site.

* * * * *